(12) United States Patent
Forest et al.

(10) Patent No.: US 10,679,755 B2
(45) Date of Patent: Jun. 9, 2020

(54) METHODS, SYSTEMS, AND COMPUTER READABLE MEDIA FOR DATA ANALYSIS AND INFERENCE OF PARTICLE DIFFUSION IN TARGET MATERIALS AND TARGET MATERIAL SIMULANTS

(71) Applicant: The University of North Carolina at Chapel Hill, Chapel Hill, NC (US)

(72) Inventors: Mark Gregory Forest, Chapel Hill, NC (US); John William Mellnik, Carrboro, NC (US); Paula Andrea Vasquez, Chapel Hill, NC (US); David Brooks Hill, Burlington, NC (US); Scott Alister McKinley, Gainesville, FL (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 601 days.

(21) Appl. No.: 14/762,657

(22) PCT Filed: Jan. 23, 2014

(86) PCT No.: PCT/US2014/012752
§ 371 (c)(1),
(2) Date: Jul. 22, 2015

(87) PCT Pub. No.: WO2014/116827
PCT Pub. Date: Jul. 31, 2014

(65) Prior Publication Data
US 2016/0004839 A1    Jan. 7, 2016

Related U.S. Application Data

(60) Provisional application No. 61/755,841, filed on Jan. 23, 2013, provisional application No. 61/767,220, filed on Feb. 20, 2013.

(51) Int. Cl.
*G16H 50/50* (2018.01)
*G09B 23/28* (2006.01)
(Continued)

(52) U.S. Cl.
CPC ............. *G16H 50/50* (2018.01); *G06F 17/16* (2013.01); *G06F 19/00* (2013.01); *G09B 23/28* (2013.01); *G09B 23/30* (2013.01)

(58) Field of Classification Search
None
See application file for complete search history.

(56) References Cited

U.S. PATENT DOCUMENTS

2001/0029957 A1   10/2001   Kwon
2010/0120077 A1   5/2010    Daridon
(Continued)

FOREIGN PATENT DOCUMENTS

AU    2014209378 B2    9/2016
CA    2899197          1/2019

OTHER PUBLICATIONS

Cu et al. "Mathematical modeling of molecular diffusion through mucus", Feb. 27, 2009, Advanced drug delivery review vol. 61 No. 2, pp. 101-114.*
(Continued)

*Primary Examiner* — Aniss Chad
*Assistant Examiner* — Robert S Brock
(74) *Attorney, Agent, or Firm* — Jenkins, Wilson, Taylor & Hunt, P.A.

(57) ABSTRACT

Methods, systems, and computer readable media for data analysis and inference of particle diffusion in mucus barriers and generic permeable biomaterials are disclosed. According to one aspect, the subject matter described herein includes a method for data analysis and inference of particle diffusion in target materials, such as mucus barriers, or their
(Continued)

simulants. The method includes collecting experimental data of observed particle movement through samples of a target material or simulant ("the target"), analyzing the collected data to determine the stochastic diffusive process that is being observed for particular particles in the particular sample, using one or more of the observed stochastic diffusive processes to simulate the diffusion of particles through layers of the target of various thicknesses, using the simulation results to determine how passage time scales according to thickness of the target, and verifying the simulation results.

22 Claims, 5 Drawing Sheets

(51) Int. Cl.
G09B 23/30 (2006.01)
G06F 17/16 (2006.01)
G06F 19/00 (2018.01)

(56) References Cited

U.S. PATENT DOCUMENTS

| | | | |
|---|---|---|---|
| 2010/0285082 A1 | 11/2010 | Fernandez | |
| 2011/0084218 A1 | 4/2011 | Duhr et al. | |
| 2011/0287948 A1 | 11/2011 | Suresh et al. | |
| 2012/0155725 A1 | 6/2012 | Bathe et al. | |
| 2013/0116935 A1* | 5/2013 | Roding | G01N 15/06 702/29 |
| 2014/0067342 A1* | 3/2014 | Calderon | G06F 17/5009 703/2 |
| 2019/0004299 A1* | 1/2019 | Kukura | G02B 21/0004 |

OTHER PUBLICATIONS

Valentine et al. "Investigating the microenvironments of inhomogenous soft materials with multiple particle tracking" 2001, Phyisical Review E, vol. 64, 9 pages.*
Fricks, John, Lingxing Yao, Timothy C. Elston, and M. Gregory Forest. "Time-domain methods for diffusive transport in soft matter." SIAM journal on applied mathematics 69, No. 5 (2009): 1277-1308 (Year: 2009).*
Kou, Samuel C. "Stochastic modeling in nanoscale biophysics: subdiffusion within proteins." The Annals of Applied Statistics 2, No. 2 (2008): 501-535 (Year: 2008).*
McKinley, Scott A., Lingxing Yao, and M. Gregory Forest. "Transient anomalous diffusion of tracer particles in soft matter." Journal of Rheology 53, No. 6 (2009): 1487-1506 (Year: 2009).*
Gaffney, Scott, and Padhraic Smyth. "Trajectory clustering with mixtures of regression models." In KDD, vol. 99, pp. 63-72. 1999 (Year: 1999).*
Beck-Broichsitter et al., "Evaluating the Controlled Release Properties of Inhaled Nanoparticles Using Isolated, Perfused, and Ventilated Lung Models," Journal of Nanomaterials, pp. 1-16 (2011) (Year: 2011).*
Didier, Gustavo, Scott A. McKinley, David B. Hill, and John Fricks. "Statistical challenges in microrheology." Journal of Time Series Analysis 33, No. 5 (2012): 724-743 (Year: 2012).*
Fischer, Russell, and Metin Akay. "Improved estimators for fractional Brownian motion via the expectation—maximization algorithm." Medical engineering & physics 24, No. 1 (2002): 77-83 (Year: 2002).*
Jeon, Jae-Hyung, Aleksei V. Chechkin, and Ralf Metzler. "First passage behavior of multi-dimensional fractional Brownian motion and application to reaction phenomena." In First-Passage Phenomena and Their Applications, pp. 175-202. 2014 (Year: 2014).*

Notification of Transmittal of the International Search Report and the Written Opinion of the International Searching Authority, or the Declaration for International Application No. PCT/US2014/012752 (dated May 14, 2014).
Ackerman et al., "Measures of Clustering Quality: A Working Set of Axioms for Clustering," Proceedings of Neural Information Processing Systems (NIPS), pp. 1-8 (2008).
Beck-Broichsitter et al., "Evaluating the Controlled Release Properties of Inhaled Nanoparticles Using Isolated, Perfused, and Ventilated Lung Models," Journal of Nanomaterials, pp. 1-16 (2011).
Chen et al., "Rheological Microscopy: Local Mechanical Properties from Microrheology," Physical Review Letters, vol. 90, No. 10, pp. 108301-1-108301-4 (2003).
Crocker et al., "Methods of Digital Video Microscopy for Colloidal Studies," Journal of Colloid and Interface Science, vol. 179, No. 1, pp. 1-12 (2012).
Dieker, "Simulation of fractional Brownian motion," Ph.D. Thesis, University of Twente, pp. 1-71 (2004).
Eixarch et al., Drug Delivery to the Lung: Permeability and Physicochemical Characteristics of Drugs as the Basis for a Pulmonary Biopharmaceutical.
Ensign et al., "Mucus Penetrating Nanoparticles: Biophysical Tool and Method of Drug and Gene Delivery," Advanced Materials, vol. 24, No. 28, pp. 3887-3894 (2012).
Fernandes et al., "Preclinical models for pulmonary drug delivery," Expert Opinion on Drug Delivery, vol. 6, No. 11, pp. 1231-1245 (2009).
Jeon et al., "First passage behavior of fractional Brownian motion in two-dimensional wedge domains," EPL, vol. 94, No. 2, pp. p-1-p-6 (2011).
Kumar et al., "Biopharmaceutics drug disposition classification system: an extension of biopharmaceutics classification system," International Research Journal of Pharmacy, vol. 3, No. 3, pp. 5-10 (2012).
Lai et al., "Mucus-penetrating nanoparticles for drug and gene delivery to mucosal tissues," Advanced Drug Delivery Reviews, vol. 61, No. 2, pp. 1-36 (2009).
Lipworth, "New perspectives on inhaled drug delivery and systemic bioactivity," Thorax, vol. 50, No. 2, pp. 105-110 (1995).
Loudet et al., "Strokes Drag on a Sphere in a Nematic Liquid Crystal," Science.
Savin et al., "Static and Dynamic Errors in Particle Tracking Microrheology," Biophysical Journal, vol. 88, No. 1, pp. 623-638 (2005).
Tibshirani et al., Estimating the number of clusters in a data set via the gap, 2001.
Communication of the extended European search report for European Application No. 14743797.4 (dated Oct. 27, 2016).
Cu et al., "Mathematical modeling of molecular diffusion through mucus," Advanced Drug Delivery Reviews, 61, pp. 101-114 (2009).
Ernst et al., "Fractional Brownian motion in crowded fluids," Soft Matter, 8, pp. 4486-4489 (2012).
Notice of Acceptance for Australian Patent Application No. 2014109378 (dated May 12, 2016).
Office Action for Canadian Patent Application No. 2,899,197 (dated Jan. 26, 2016).
Communication of European publication number and information on the application of Article 67(3) EPC for European Patent Application No. 14743797.4 (dated Nov. 4, 2015).
Office Action for Australian Patent Application No. 2014209378 (dated Oct. 16, 2015).
Crater et al., "Barrier Properties of Gastrointestinal Mucus to Nanoparticle Transport," Macromolecular Bioscience, vol. 10, pp. 1473-1483 (2010).
Notice of Allowance corresponding to Canadian Application Serial No. 08932194CA dated Jun. 4, 2018.
Office Action corresponding to Canadian Patent Application No. 2,899,197 dated Apr. 19, 2017.
Communication persuant to Article 94(3) EPC for European Patent Application Serial No. 14 743 797.4 (dated May 29, 2019).

* cited by examiner

METHODS, SYSTEMS, AND COMPUTER READABLE MEDIA FOR DATA ANALYSIS AND INFERENCE OF PARTICLE DIFFUSION IN TARGET MATERIALS AND TARGET MATERIAL SIMULANTS

PRIORITY CLAIM

This application claims the benefit of U.S. Provisional Patent Application Ser. No. 61/755,841, filed Jan. 23, 2013 and U.S. Provisional Patent Application Ser. No. 61/767,200, filed Feb. 20, 2013, the disclosures of which are incorporated herein by reference in their entireties.

GOVERNMENT INTEREST

This invention was made with government support under Grant No. DMS-1100281 awarded by the National Science Foundation. The government has certain rights in the invention.

TECHNICAL FIELD

The subject matter described herein relates to predictive tools of clinical and medical relevance relating to the movement of 0.1-10 micron diameter particles in pulmonary mucus and related complex biological materials, such as cells, tissue, blood clots, and gel patches for controlled drug release. More particularly, the subject matter described herein relates to methods, systems, and computer readable media for data analysis and inference of particle diffusion in mucus barriers or any biological material where diffusive penetration of particles requires quantitative estimation.

BACKGROUND

The quantification of foreign particle transport, including heterogeneity in particle diffusion, is necessary for the development of effective transmucosal drug delivery methods, and more generally of particle penetration through biological structures and synthetic gels. Every organ, as well as the eyes, nasal tract and female reproductive tract, is protected by a layer of mucus. It is increasingly recognized that transmucosal delivery is a pathway for treating disease throughout the entire body. Pulmonary drug delivery is of particular interest because it has been shown to lead to a direct targeting of the drug carrier load to epithelial cells (e.g., for lung cancer) and immense lung vasculature, to a reduction in side effects, to faster drug onset times, and to controlled release times of drugs from carrier particles by tuning diffusion timescales relative to carrier particle drug release timescales. Inhalation has been identified as a potentially superior method of drug delivery for a range of conditions such as chronic obstructive pulmonary disease (COPD), asthma and cystic fibrosis, and lung cancer. Inhalation has also been proposed as a delivery mechanism for vaccines, gene therapies, and insulin.

Despite the benefits and wide range of potential applications, the results of clinical transmucosal-based treatments have been mixed for a variety of reasons, e.g., inconsistencies in understanding and measurement of drug uptake. A poor quantitative understanding of drug carrier particle transport in and through the mucus barrier is a key factor for these inconsistencies. Mucus concentration (determined by % solids including a spectrum of mucins, salts, and proteins, and a measure of airway liquid hydration) varies dramatically across organs but also between samples taken from the same organ. Within the gastrointestinal tract, for example, the thickness and physical properties of the mucus layer vary by location as well as diet. Mucus properties in the lung are similarly variable with mucus layer thickness ranging from a small fraction of a micron ($\mu$m) to 50 $\mu$m depending on location in the lung and many other factors (chronic cough, for example). Mucus concentration likewise varies with age, disease progression, and across populations. Diseases such as cystic fibrosis and COPD cause the physical properties of mucus to change dramatically during disease progression.

Due to this high variability, it has been difficult to accurately control drug residence time in the mucosal layer relative to the chemical degradation of the carrier particle and relative to the innate clearance time of the mucus layer. The key information about passage times through the mucosal layer to reach epithelial tissue and vasculature is poorly understood, and thereby typically not addressed in drug delivery estimates. This is further exacerbated by the fact that drug inhalation particles are often tested on animal models prior to clinical trials, adding further variability and making it difficult to interpret results. Several years ago, the need to quantify the differences in transmucosal drug penetration between parts of the body as well as diseased and healthy states was recognized, but progress has been slow due to the complexity of the required experiments and the lack of progress on rigorous analysis of experimental data.

Conventional approaches to modeling particle diffusion through mucus layers use observed data to determine the effective viscosity of a fluid, and infer an effective diffusion coefficient over the timescale of the experiment. The industry standard method for determining a particle's diffusivity in mucus involves calculating the mean squared displacement (MSD) and this value is often reported as a fraction of the diffusivity of that particle in water. In other words, there is an assumption that the MSD of a particle undergoing Brownian motion scales linearly with time, a behavior which is herein referred to as "normal" diffusion behavior. While this provides a useful benchmark for comparing diffusion rates versus particle size, shape and surface chemistry, it is a simplification with unquantifiable errors of the underlying complexity in the system. Determining the diffusivity from the pre-factor of the MSD assumes that the diffusion process can be described by a single diffusion coefficient, and that the MSD is linear in time.

Research has shown, however, that the MSD of a particle traveling through human lung mucus, for example, does not obey simple diffusion processes and does not scale linearly with time, but in fact scales more slowly than would be expected for normal diffusion, behavior which is herein referred to as "scaling sub-diffusively". The data reveal that micron diameter particles in mucus exhibit sub-diffusive behavior, with a fractional power of lag time rather than scaling linearly in time. As a result, any model that is based on the assumption of normal diffusion of particle through human lung mucus will not accurately represent the behavior of real mucus. For normal diffusion, one can rigorously infer how passage time distributions scale with the thickness of the layer being penetrated; for sub-diffusive processes, there is no method known in the prior art to determine how passage times depend on layer thickness, and it therefore must be estimated by alternative methods presented below. This is problematic for medical treatments that use inaccurate diffusion models to calculate dosing, for example, especially since the complex viscosity of the mucus layer changes as the disease progresses or in response to treatment, and since layer thicknesses are variable within lung airways.

Another problem with conventional approaches to modeling particle diffusion through mucus layers is that the mucus is assumed to have a uniform characteristic throughout. That is, one can ascribe an average diffusivity and any predictions about particle transport will be accurately approximated on this basis. In reality, mucus layers may have channels through which particles quickly pass through the mucus layer to the underlying tissue and vasculature, and mucus layers may have pockets of highly contrasted physical properties, which tend to capture and sequester particles within the mucus layer. It is therefore critical to assess the likelihood of outlier particles that exhibit both the fastest and slowest passage times, and to quantitatively estimate those passage times. Clearly, since normal or simple diffusion processes do not accurately model sub-diffusion through homogeneous mucus and similar biomaterials, the situation is magnified in the presence of heterogeneity. Current predictions of passage times through mucosal layers, and their scaling with layer thickness, based on simple diffusion processes, are consequently highly inaccurate. As a result, any model that assumes that all similar particles travel through the mucus at the same normal diffusion rate will not accurately reflect the behavior of particles in real mucus, and in fact the errors made in such estimates are unquantifiable without an alternative, rigorously based, protocol. Such a protocol is the basis of this application.

These types of issues play a direct role in the inconsistencies between theoretical and experimental drug uptake. Because the current standard methods do not accurately describe how sub-micron to several micron diameter particles diffuse in mucus and other biofluids, biogels, blood clots, etc., it has been difficult to determine what percent of a drug will make it through the mucus barrier or related biological layer, and therefore difficult to determine what effective dose has reached the target relative to other timescales (mucus clearance, particle degradation). In order to better describe the drug uptake process, it is highly desirable to accurately determine the passage times of particles traversing the mucosal layer as a function of layer thickness.

Accordingly, in light of these disadvantages associated with conventional approaches for determining a particle's diffusivity in mucus, there exists a need for more accurate methods. More specifically, there is a need for methods, systems, and computer readable media for data analysis and inference of particle diffusion in mucus barriers.

SUMMARY

According to one aspect, the subject matter described herein includes a method for data analysis and inference of particle diffusion in target materials, such as mucus barriers, more general biological materials, non-biological materials, and synthetic, permeable materials, as well as simulants of the above. The method includes collecting experimental data of observed particle movement through samples of a target material, analyzing the collected data to determine the stochastic diffusive process that is being observed for particular particles in the particular material sample, assessing heterogeneity across the particle ensemble, using one or more of the observed stochastic diffusive processes to simulate the diffusion of particles through the material, using the simulation results to determine how passage time scales according to thickness of the target material, and verifying the simulation results against the experimental data or with a subsequent validation experiment. The method may be applied not only to target materials but also to target material simulants, which are materials that simulate, imitate, or approximate the behavior of a target material. Target material simulants may be synthetic or engineered materials, and may be natural materials. Target material simulants need not reproduce all characteristics of the corresponding target material (but they may.) As used herein, the phrase "target material" means "target material or target material simulant" unless otherwise indicated.

As used herein, the term "stochastic" means "having a random probability distribution or pattern that may be analyzed statistically but may not be predicted without ascribing likelihood of a particular outcome; of or pertaining to a process involving a randomly determined sequence of observations each of which is considered as a sample of one element from a probability distribution." A "stochastic process", in other words, is non-deterministic, involving an element of chance or randomness.

As used herein, the term "Hurst parameter" is a parameter measuring the correlation between increments of a stochastic process. The Hurst parameter is denoted by the variable H. When H>0.5, there is an infinite span of interdependence between the intervals, i.e. every increment is correlated with every other increment. H>0.5 corresponds to super diffusive behavior in which a particle undergoing passive thermal diffusion has a tendency to move in the same direction. H<0.5 corresponds to sub-diffusive behavior in which the displacements are negatively correlated. H=0.5 indicates that the there is no correlation in the increments which corresponds to regular Brownian motion. In certain fields, the variable $\alpha$ is often used to replace H. There is a simple equation which relates the two, $\alpha=2H$.

According to another aspect, the subject matter described herein includes a system for data analysis and inference of particle diffusion in and through mucus barriers, analogous layers (e.g., a drug release membrane) and other complex fluids that may be applied over time to assess and treat disease progression. The system includes a data storage device for storing collected experimental data of observed particle movement through samples of a target mucus, and a hardware processor for analyzing the collected data to determine the stochastic diffusive process that is being observed for particular particles in the particular mucus sample, using one or more of the observed stochastic diffusive processes to simulate the diffusion of particles through mucus layers of various thicknesses, using the simulation results to determine how passage time scales according to thickness of the mucus or other barrier layer, and verifying the simulated results against the experimental data. These tools can be applied to patients over a time course to detect changes in mucus physical properties, to assess efficacy of drug or physical therapies, and to assess disease progression.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform prescribed steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings, wherein like reference numerals represent like parts, of which.

DETAILED DESCRIPTION

Figure 1:
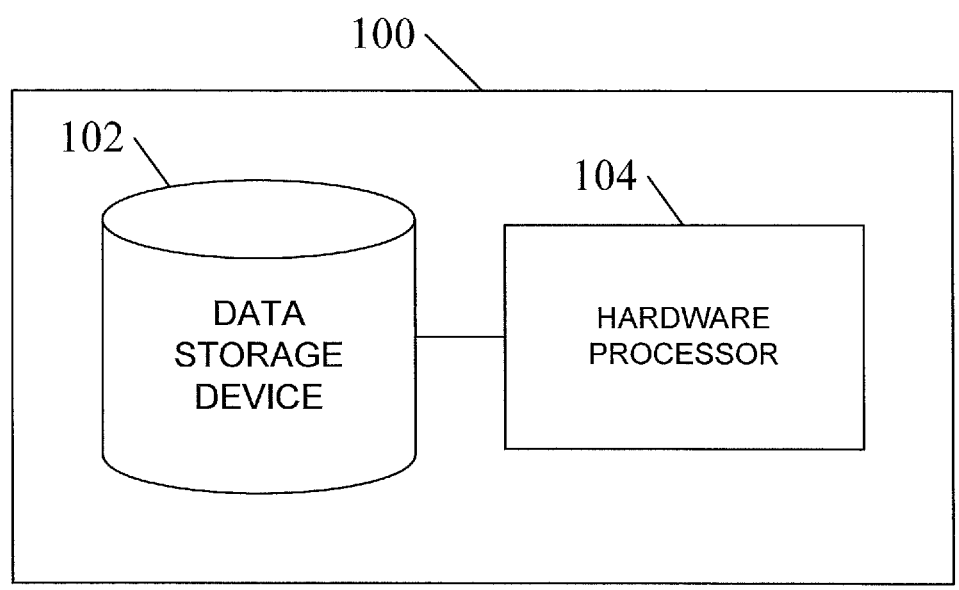
FIG. 1 is a block diagram illustrating an exemplary system for data analysis and inference of particle diffusion in mucus barriers and generic permeable biomaterials according to an embodiment of the subject matter described herein.

In accordance with the subject matter disclosed herein, systems, methods, and computer readable media are provided for data analysis and inference of particle diffusion in mucus barriers or related biofluids and simulants. The subject matter described herein provides a method to detect and distinguish populations of particles experiencing statistically distinct diffusion processes. A sub-diffusive process, which is not assumed to be simple diffusion, is then fit to each population and used to model the mean passage time as a function of layer thickness. Numerical simulations of particle diffusion allow for a reduction of the current reliance on animal models, which are both expensive and limited in their applicability to human tests. These techniques also have the ability to reduce the cost of administering and supplying transmucosal drugs by increasing delivery efficiency. Better understanding of how heterogeneity impacts drug uptake allows optimization of drug design for very specific parts of the body, thereby reducing the amount of a drug trapped in the mucosal layer. It would also be possible to tailor drug delivery mechanisms to specific diseases or a patient's physical state in order to increase drug delivery effectiveness. The customization of drug delivery through transmucosal membranes at this level is unprecedented.

The subject matter described herein overcomes the disadvantages suffered by conventional approaches by collecting experimental data and also identifying statistically significant clustering of data into distinct populations, according to the particles' observed behavior. Each distinct cluster—rather than particle—is characterized. For example, the Gaussian parameters defining each cluster may be determined. In this manner, the motion of a large number of particles may be simulated using the parameters of the cluster of which that particle is a member. The simulated paths created by the moving particles may then be analyzed to determine the passage time distribution through the mucus layer associated with each cluster of particles for a known layer thickness, and through comprehensive numerical simulations the scaling with respect to mucus layer thickness of each cluster passage time distribution may be computed.

This approach has several advantages over conventional methods. For example, where the mucus layer has non-uniform characteristics, such as the channels and pockets described above, this will result in multiple clusters of particles being identified—i.e., a cluster that represents the probability of fast outlier particles that diffuse through the most permeable pathways in the mucus layer, together with the passage times associated with those fast outliers, another cluster that represents the likelihood and passage time distributions of the slowest outlier particles that have been sequestered in a pocket within the mucus, a third cluster that represents the likelihood and behavior of a particle that has intermediate passage time distributions between the fastest and slowest outliers. This approach goes beyond conventional methods both in quantifying distributions of particle passage times rather than some mean passage time estimate, and in quantifying distinct clustering of particles associated with mucus heterogeneity. Taken together, this approach addresses full statistical estimates of passage times and residence times in a given mucus sample by a specific particle load as a function of mucus layer thickness.

Another advantage is that, once the stochastic processes are identified and modeled separately, extensive simulation may be performed to generate a large enough number of simulated paths from which clinically relevant factors, such as survival time and first passage time distributions may be extracted, thus obviating the need for expensive and time consuming empirical studies. The validity of the simulations can be easily verified using the same experimental data collected in the first step or subsequent validation experiments. Furthermore, where multiple stochastic processes are identified by observation, the simulations performed may model a subset of the identified stochastic processes, where the subset contains one, some, or all of the identified stochastic processes. In one embodiment, simulation may use the process or processes selected according to a best fit algorithm, although other selection criteria may also be used.

FIG. 1 shows an exemplary system for data analysis and inference of particle diffusion in mucus barriers and generic permeable biomaterials according to an embodiment of the subject matter described herein. In embodiment illustrated in FIG. 1, system 100 includes a data storage device 102 for storing collected experimental data of observed particle movement through samples of a target mucus, and a hardware processor 104 for analyzing the collected data to determine at least one stochastic diffusive process that is being observed for particular particles in the particular mucus sample, using the at least one observed stochastic diffusive processes to simulate the diffusion of particles through the target mucus, using the simulation results to determine how passage time scales according to thickness of the target mucus or other barrier layer, and verifying the simulation.

Figure 2:
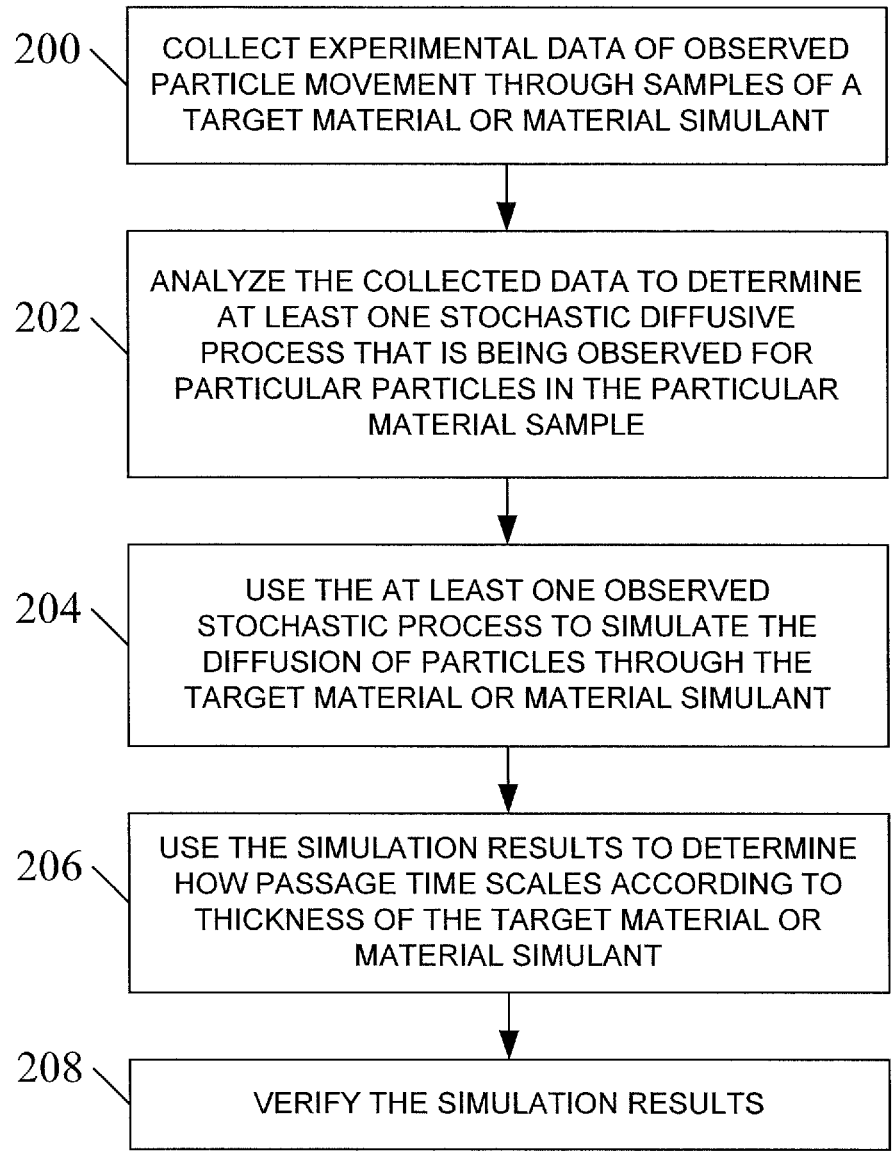
FIG. 2 is a flow chart illustrating an exemplary process for data analysis and inference of particle diffusion in mucus barriers and generic permeable biomaterials according to an embodiment of the subject matter described herein.

FIG. 2 is a flow chart illustrating an exemplary process for data analysis and inference of particle diffusion in mucus barriers and generic permeable biomaterials according to an embodiment of the subject matter described herein.

At step 200, experimental data of observed particle movement through samples of a target material, which may be a mucus barrier, a gel, a generic permeable biomaterial, etc. At step 202, the collected data is analyzed to identify one or more stochastic diffusive processes being observed for the particular particles in the particular material sample. At step

204, the one or more stochastic processes that were observed are used to simulate the diffusion of particles through the target material. At step 206, the simulation results are used to determine how passage time scales according to the thickness of the target material. At step 208, the simulation results are verified.

DETAILED EMBODIMENTS

The subject matter described herein prescribes an experimental-theoretical protocol, where the experiments may be performed with commercially available instruments and the theoretical component may be performed with software provided in this methods and systems described herein. This protocol is applicable to any fluid, including but not limited to mucus barriers, from lung airways, intestinal organs, and female reproductive tract, and any specific particle that can be tracked with microscopy. The product or output of this protocol is a rigorous prediction of the distribution of passage times of the particles of interest through the mucus barrier of interest, with a precise estimation of how the passage time distributions vary and scale with thickness of the mucus barrier. The subject matter described herein comprises four distinct steps: experimental data collection, data analysis, simulation of passage time scaling with sample thickness, and experimental verification. Each of these steps is described in detail in the following document. The novelties of this protocol include: the synthesis of the four steps; the data analysis applied to particle diffusion in mucus, including detection and characterization of heterogeneity on scales larger than the particle diameter; the simulation of passage times and their scaling with mucus layer thickness, using model inference results from the data analysis step; and, the experimental verification that cross-checks steps I and III.

I. Experimental Data Collection

In one embodiment, experimental data may be collected in the following manner. Between 2 microliters and several milliliters (ml) of mucus is infused with the particles of interest. Standard video microscopy techniques are then used to extract positional data at discrete time intervals from 0.05 ml of the sample at a time. For example, a Nikon Eclipse TE2000-U at 40× magnification may be used for particle imaging together with particle tracking software. The frame rate and total tracking time may be specific to the fluid and particles of interest.

II. Data Analysis

The current industry standard is to rely on the relationship between the generalized Stokes-Einstein relation (GSER) and the mean squared displacement (MSD) of a particle undergoing Brownian motion to determine the effective viscosity of a fluid. The protocol presented herein exploits the standard methods to gather data while completely abandoning the use of that data for viscoelastic inference. Instead, the data is used to analyze the stochastic diffusive process that is being observed for that particular particle in that particular mucus sample. The industry standard for particle diffusion through mucus layers is to infer an effective diffusion coefficient over the timescale of the experiment. This approach leads to uncontrollable errors since particle diffusion in mucus and other complex fluids is anomalous and sub-diffusive and the mucus layer itself is heterogeneous. For example, fitting a diffusion coefficient to anomalous sub-diffusive processes will yield a different diffusion coefficient for every total timescale of the process.

In one embodiment, the first step in the analysis is to study the bead increments (displacements), and to determine whether they are Gaussian, a sum of Gaussians, or neither. Given micro-particle path data obtained from step I, analysis is performed on the per-particle paths (or path segment) standard deviation of the step size distributions (also known as the van Hove correlation function) in order to identify a statistically significant clustering of the data into a discrete set of distinct populations. While the following protocol is focused on the standard deviation of step sizes, any path metric can be substituted here. Other potential path metrics include, but are not limited to, the variance, median displacement, maximum displacement, skewness, and interquartile range. Each statistic of choice may be calculated for the entire path of a particle or a path segment. When using the standard deviation as the statistic of choice, this analysis is valid for any fluid for which diffusion within has the generic property that the distribution of increments of an individual bead is normally distributed (i.e., Gaussian). Different choices of statistic may be better suited for different distributions of the van Hove correlation function.

Consider a vector containing m observations, $$\mathbb{X} = \begin{bmatrix} x_1 \\ x_2 \\ \vdots \\ x_m \end{bmatrix}$$

where each $x_i = [x_i^1, \ldots, x_i^b]$. Our current data acquisition system has the capacity to collect data on the X, Y, Z positions, and yaw, pitch and roll variables such that $x_i \in \mathfrak{R}^{1 \times 6}$; however in our current analysis we focus on the position in the X-Y plane, ignoring the other features. In order to calculate the displacements from the position vector X while controlling for the overlap between the intervals, we introduce two new variables, displacement length (DL) and displacement gap (DG). Given X we can calculate the displacement vector as follows.

$$D = \begin{bmatrix} d_1 \\ d_2 \\ \vdots \\ d_n \end{bmatrix}$$

For $d_k$, $k \in \{1:n\}$, let $d_k = x_{i_k} - x_{j_k}$. Given $j_1 = 1$, the elements of vector D are defined in terms of the recursive relation $$i_k = j_k + DL$$

$$j_k = i_{k-1} + DG + 1, k \geq 2$$

The DL parameter sets the length over which a displacement is calculated and the DG parameter effectively determines the overlap, or the number of data points that are incorporated into multiple $d_i$ values. Our standard notion of displacement, $d_i = x_{i+1} - x_i$ is given by DG=0, DL=1, which are the minimum values for each parameter. For a given set of data, we will adopt the notation $D_p(DG,DL)$ to indicate the parameters with which the displacement vector was calculated.

Figure 3:
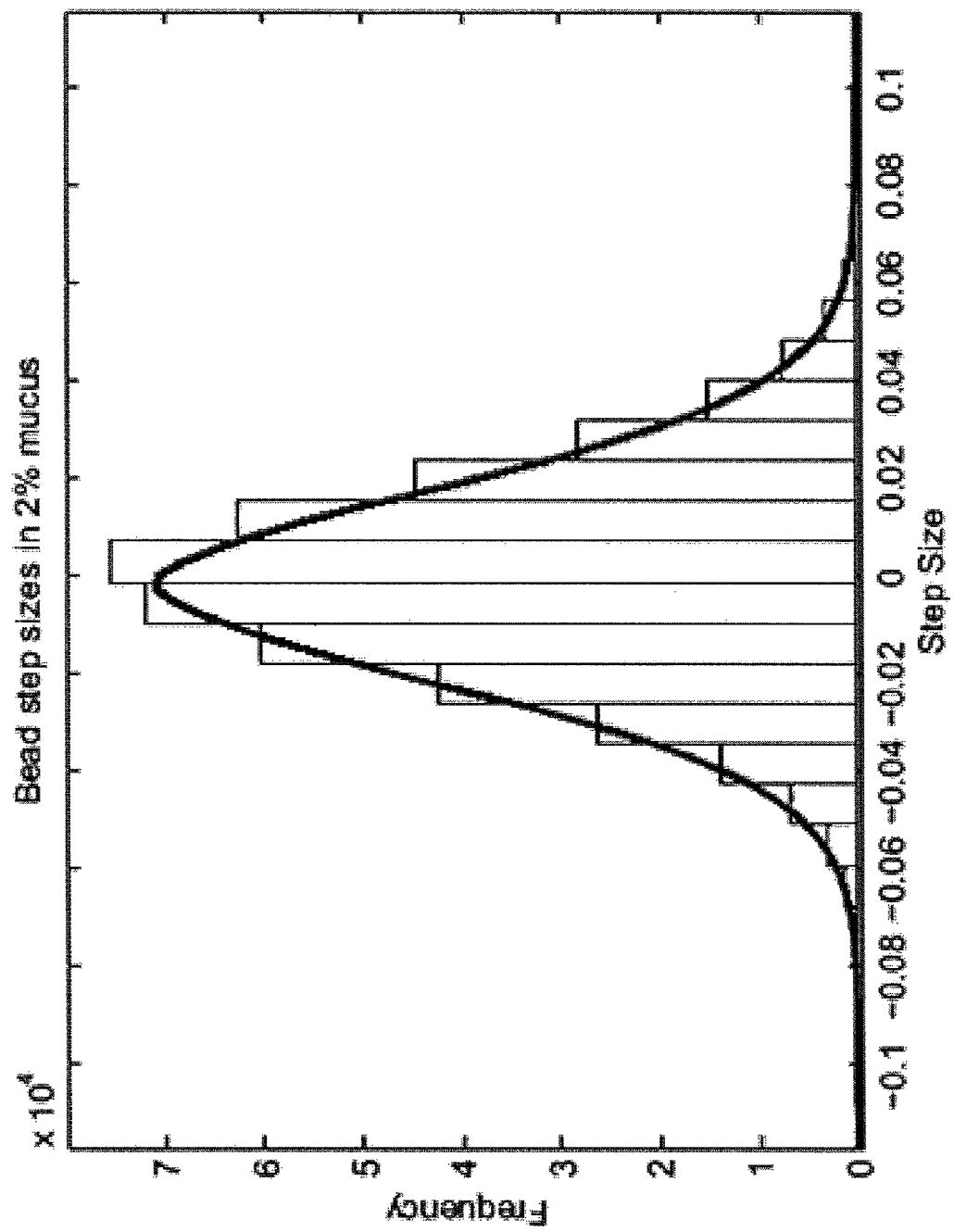
FIG. 3 is a graph illustrating that displacement of a particle diffusing in mucus follows an approximate Gaussian distribution.

FIG. 3 is a graph illustrating displacement of a particle diffusing in mucus. As can be seen in FIG. 3, which shows experimental step size distribution $D_p(0, 1)$ of 260 1 μm particles diffusing in 2 wt % (of solids) mucus, the displacement $D_p(0, 1)$ of a particle diffusing in 2 wt % mucus follows an approximate Gaussian distribution.

For a single particle initially located at position p=0 and undergoing one dimensional normal diffusion, its mean position is always p=0. We now give an illustration of statistical analyses for normal diffusive processes, inserting new steps into the analysis to anticipate heterogeneity and to lay the classical foundation before explaining the subject matter described herein for analysis and inference of sub-diffusive processes typical of mucus and many other biomaterials. It is well known that the function describing the probability of the particle being in the interval (p,p+dp) at time t can be described by a Gaussian of the form $$P(p)dp = \frac{1}{(2\pi Dt)^{\frac{1}{2}}} e^{-\frac{p^2}{4Dt}} dp \qquad (1)$$

Whereas most previous work has centered on the MSD as a measure for the spread of this probability density function and therefore the diffusivity, we use the direct calculation of the standard deviation of a particle's displacement over a set time Δt. If the total time t a particle is observed diffusing over is divided into discrete intervals of size Δt, equation (1) may be applied to each of these intervals. The difference in positions at the beginning and end of an interval will be equal to the average displacement of the particle over that interval. Let Y(t) represent an observation of the location of a particle at time t. Equation (1) implies that Y(t) is a random variable that can be expressed as $$Y(t) = \sqrt{2D\Delta t} dW_1 + \epsilon dW_2$$

where $dW_1$ and $dW_2$ are independent standard normal random variables (i.e. having mean 0 and variance 1) and $\epsilon$ parameterizes the magnitude of the error due to both static and dynamic experimental error.

According to the Stokes-Einstein equation, diffusivity is inversely proportional to both the viscosity of the diffusing particle and the particle's radius.

$$D = \frac{k_B T}{6\pi\eta r} \qquad (2)$$

where $k_B$ is Boltzmann's constant and T is temperature.

The standard deviations of the displacements may be found through direct calculation. The introduction of $D_p(DG, DL)$, allows control of the number of data points that are to be incorporated into each displacement and the time scale over which the analysis is performed.

Once the standard deviations of the step size distributions for each particle path or path segment have been calculated, it is possible to look for populations of particles with similar standard deviations. While standard clustering techniques such as K-means or K-medoids clustering may be used, an embodiment will be presented that focuses on agglomerative hierarchical clustering with the average linkage function and the Euclidean distance metric. Other potential linkage functions include, but are not limited to, Centroid, complete, median, single, ward, and weighted functions. Likewise, other potential distance metrics include, but are not limited to, Standardized Euclidean, city block, Minkowski distance, Chebychev distance, Mahalanobis distance, cosine, correlation, Spearman distance, Hamming distance, Jaccard distance, and others. This allows the construction of a dendrographic representation of the data for a given time scale $\tau$, which shows the similarity between groups of points at different length scales.

It is noted that $\tau$ has units of time. In one embodiment, the code may be implemented in "steps" by relying on a variable DL (instead of $\tau$), which is related to $\tau$ by the equation $\tau = DL*f$ where f is the temporal resolution of the data.

Several different objectives can guide the initial clustering process. In one embodiment, a clustering may be desired which maximizes the heterogeneity in the data over all choices of $\tau$, a subset of $\tau$, or at a specific $\tau$. In one embodiment, a clustering may be desired which captures the heterogeneity at a time scale proportional to the expected mean passage time of the particles though a layer of a given thickness.

In order to create a disjoint clustering of the data, a cutoff length scale Cut at which to cut the dendrogram and partition the data into $K_{Cut}$ clusters may be chosen. The value Cut determines the partitioning of the data, and its importance is often overlooked when using hierarchical clustering techniques. Whereas Cut is often chosen based on a preexisting knowledge of the number of clusters in the data, the methods and systems disclosed herein approach this task with no prior knowledge of Cut. In one embodiment, variable Cut is chosen such that $K_{Cut}$ takes on the values 1, 2, 3, . . . , $K_{max}$, which span the clustering possibilities from 1 to $K_{max}$ clusters, where $K_{max}$ must be less than N, the number of observed paths or path segments. The next step is to identify the optimal $K_{Cut}$ based on a measure of clustering quality. For this step, axioms of clustering quality metrics may be applied. There are many metrics, including, but not limited to, weakest link and additive margin cluster quality metrics, that have been proposed to gauge the quality of a clustering, any of which may be substituted here. Without loss of generality we will use the $$W_{Cut} = \sum_{r=1}^{K_{Cut}} \frac{1}{2n_r} D_r^\nu \qquad (3)$$

where $n_r$ is the number of elements in cluster r and $D_r$ is the sum of the pairwise Euclidean distances between all the elements of cluster r. The parameter $\nu \in (-\infty, \infty)$ weights the within-cluster contribution to $W_{Cut}$. When $\nu=1$, Eqn. (3) gives the within-cluster sum of squared distances from the respective cluster means. As the number of clusters increases, $W_{Cut}$ decreases. The next step is to determine the optimal value of Cut, and therefore the optimal number of clusters. Following the same reasoning for K-means clustering, we assume that there are precisely K* clusters in our data. As we decrease $K_{Cut}$ for $K_{Cut} < K^*$, the natural divisions in the data are the first to be found when partitioning the data, producing significant decreases in $W_{Cut}$. Once $K_{Cut} > K^*$ we are partitioning groups of points which are naturally similar to each other, therefore producing much smaller drops in $W_{Cut}$ as $K_{Cut}$ further increases. We are interested in how $W_{Cut}$ changes relative to $W_{ref}$, calculated from the clustering of a data set of the same size that is distributed over the sample space according to a well-defined PDF. The log difference, $\log(W_{ref} - W_{Cut})$, is known as the gap statistic and has been shown to be an accurate method for determining the number of natural divisions in a data set. Two other metrics, the non-logarithmic gap statistic, $W_{ref} - W_{Cut}$, and the slope-gap statistic, $W'_{ref} - W'_{Cut}$ may be substituted for the gap statistic depending on the desired sensitivity of the results and the type of data being analyzed.

The reasoning in the previous paragraph is based on the assumption that the natural divisions in the data are the first to be found when decreasing $K_{Cut}$. When outliers are present in the data, this assumption no longer holds resulting in an underestimation of K*. Various techniques can be used to identify outliers prior to the use of agglomerative hierarchical clustering and different techniques may be used to deal with the reincorporation of these data points back into the data set. One technique is to identify outliers by selecting points with which the probability of generating them from a PDF conditioned on the ensemble data set falls below some threshold. Once identified, the outliers may either be temporarily removed ("blinked") from the dataset and reassigned after the clustering has taken place to the nearest cluster, or the outliers may be duplicated a specified number of times. Duplication in this manner changes outlying points to outlying clusters which can then easily be identified by the algorithm. The choice between the blinking outlier and duplicated outlier techniques will depend on the desired sensitivity of the algorithm among other factors.

The clustering of the data is only used to determine $K_{Cut}$, the number of partitions in the data at a specific time scale τ, not to assign particles to clusters. The clustering technique, such as hierarchical clustering as described above, is repeated for each of the time scales of interest. Once the optimal value of τ and the corresponding value of Cut is determined, we seek the underlying functions, which describe the distribution of the path metrics (i.e. standard deviations) within each partition. Various well known statistical techniques can be used to determine the PDFs which best fit each cluster. Without loss of generality, we will consider the case in which an Expectation Maximization algorithm is used to fit the PDFs and all clusters are adequately described by a Gaussian distribution; therefore we seek to determine the parameters of the Gaussian functions whose sampling most likely generated the clusters and the probability with which each particle is a member of each cluster. The sum of the probabilities of a single particle belonging to each cluster must be equal to one. A particle is assigned to a cluster if the probability of it being in that cluster is larger than the probability of it being in any other clusters. To determine these probabilities, we apply a Gaussian mixture model where the number of Gaussians is equal to the number of partitions in the data found during the cluster analysis. Each component of our model is a Gaussian of the form $$f(s|\mu,\Gamma) \propto \exp[-\tfrac{1}{2}(s-\mu)^T \Gamma^{-1}(s-\mu)] \quad (4)$$

where s is our input vector of standard deviations. There is no closed form solution to this fitting process, so we use an iterative expectation-maximization (EM) algorithm. The EM algorithm determines the parameters of the Gaussians, which best fit our distribution of data by maximizing the log likelihood of generating our data given a set of parameters for our Gaussians. If $\mu_c$ and $\Gamma_c$ are the mean and covariance for cluster c, $\pi_c$ is the proportion of particles in cluster c, subject to $$1 = \sum_{c=1}^{K_{Cut}} \pi_c$$

and N is the total number of particles or particle path segments, the log likelihood of the data given the set of Gaussian parameters is $$LL(\mu,\Gamma,\pi,s) = \sum_{i=1}^{N} \log \sum_{c=1}^{K} f(s_i|\mu_c,\Gamma_c)\pi_c \quad (5)$$

For a vector of cluster assignments, $A \in \mathbb{R}^{N \times 1}$ obtained from the clustering step, we initialize μ, Γ, π it as follows:

$$u_c = \overline{\{s_i\}}$$

$$\sum_c \mathrm{cov}(\{s_i\}), \{\forall\, i: |\{A_{i=c}\}| \geq n_{min}\}$$

$$\pi_c = \frac{|\{A_{i=c}\}|}{|A|}$$

Where $n_{min}$ is the minimum cluster size and $A_{i=c}$ is the set of points $s_i$ in cluster c. If $h_c$ is the true cluster membership of $s_i$, then our expectation step is given by $$q_{ic} = P\!\left(h_i = c \mid s_i, \mu_c, \sum_c, \pi\right) = \frac{\pi_c f\!\left(s_i \mid u_c, \sum_c\right)}{\sum_{j=1}^{K} \pi_j f\!\left(s_i \mid \mu_j, \sum_j\right)} \quad (6)$$

The parameters of $\mu_c$, $\Sigma_c$, and $\pi_c$ are then updated.

$$\mu_c^{new} = \frac{1}{\sum_{i=1}^{N} q_{nc}} \sum_{i=1}^{N} q_{ic} s_i \quad (7)$$

$$\sum_c^{new} = \frac{1}{\sum_{i=1}^{N} q_{ic}} \sum_{i=1}^{N} q_{ic}(s_i - \mu_c^{new})(s_i - \mu_c^{new})^T \quad (8)$$

$$\pi_c^{new} = \frac{\sum_{i=1}^{N} q_{ic}}{N} \quad (9)$$

$$\text{subject to } \left\{ s_i \in s : \forall\, i \left| \sum_{c=1}^{K} q_{ic} > \phi \right. \right\} \quad (10)$$

where ϕ is a cutoff threshold for continued inclusion in the iterative fitting process. The parameter ϕ may either be static, i.e. a constant, or defined in such a way that it is a dynamic variable, e.g. changing as a function of the number of iterations of the fitting algorithm. The purpose of this variable is to prevent a PDF from collapsing onto a single point. Collapse occurs when outliers are present in the data. In the example above, these outliers are not incorporated into the initialization of the Gaussian components, indicating that, initially, each outlier has a low probability of being generated by all of the components. The parameter ϕ is the threshold probability below which we choose to discard outliers.

III. Simulation of Passage Time Scaling

After each particle has been assigned to a cluster and the parameters defining each cluster have been determined, we simulate data by drawing standard deviations from each PDF in accordance with the mixing parameters $\pi_c$. The path metric of choice is then used to determine the parameters of best fit for a model of the underlying stochastic process. In this example, and without loss of generality, we choose to apply a fractional Brownian motion model. Our path metric, the standard deviations, are then converted into Hurst parameters for the purpose of simulating fractional Brownian motion. For normal diffusion, the Hurst parameter is exactly known, and furthermore there are rigorous theorems on passage time distributions and their scaling with respect to layer thickness. For sub-diffusion, there are no such results and a comprehensive direct numerical simulation of the best-fit fractional Brownian motion process is the only estimation tool. When investigating the diffusion of particles through the mucosal layer, we can take advantage of the fact that the dimensions of the mucosal layer in the sagittal and coronal planes are significantly larger than the lateral width of the mucosal layer in the transverse plane, allowing us to employ periodic boundary conditions in all but the transverse plane, simplifying our simulations from 3D to 1D. While the diffusion of a particle through the mucosal layer is a 3D process, only the diffusion in the transverse dimension is of importance for determining first passage time distributions. Let $\xi^H(t_i)$ be fractional Gaussian noise with mean zero and autocorrelation, $$\langle \xi^H(t_1)\xi^H(t_2) \rangle = 2D_{fbm}H(2H-1)|t_1-t_2|^{2(H-1)} + 4D_{fbm}H|t_1-t_2|^{2H-1}\delta(t_1-t_2). \quad (11)$$

The values of $\xi^H(t_i)$ will be calculated using one of several documented techniques. Example techniques include, but are not limited to, the Hosking method, the Cholesky method, the Davies and Harte method, the stochastic representation method, aggregation packet processes, conditionalized random midpoint displacement, spectral simulation, the Paxson method, and wavelet-based simulation. In one embodiment, the method uses the factorization of the covariance matrix. $D_{fbm}$ is the value of the anomalous diffusion coefficient. Our initial condition is $y(t_0)=L$, where L is the width of the mucosal layer. The position $y(t_{i+1})$ of a particle at $y(t_i)$ is:

$$y(t_{i+1})=y(t_i)+\xi^H(t_{i+1}) \quad (12)$$

Subject to boundary conditions, $$y(t_{i+1})=2L-y(t_i)-\xi^H(t_{i+1}) \text{ if } y(t_i)+\xi^H(t_{i+1})>L$$

$$y(t_{i+1})=0 \text{ if } y(t_i)\leq 0 \quad (13)$$

Mean field theory allows decoupling of particle-particle interactions in equation (12), leading to a trivial parallelization of the computation of particle trajectories. A large number of simulated paths can be generated which mimic the dynamics of the actual particles diffusing through the sample. From the simulated data, we can determine important clinically relevant factors such as the survival and first passage time distributions as well as hitting probabilities. The scaling behavior of the passage time distributions with fluid layer thickness is determined by post-processing the simulated data.

IV. Experimental Verification

After the simulated data has been used to produce estimates for the factors of interest, the experimental data obtained in part I is used to verify these results. First passage times can be calculated from the experimental data by defining two linear, arbitrarily oriented parallel absorbing boundaries at a distance −L and L from the initial position of each particle. The time for the particle to reach either absorbing boundary is equivalent to half the first passage time for the single absorptive boundary case. The survival function can be verified by calculating the number of particles at each time step that have not yet reached either of the absorbing boundaries. Hitting probabilities can be verified by calculating relative likelihood of reaching the −L boundary versus the L boundary. While the experimental data serves to check our predictions, these data in and of themselves are insufficient to reliably determine the survival and first passage time functions. Determining these parameters directly from experimental data would require a large amount of the sample of interest and an excessive amount of time. By collecting only the data needed to accurately create simulated data, it is possible to profile small amounts of a sample in a short amount of time.

Figure 4:
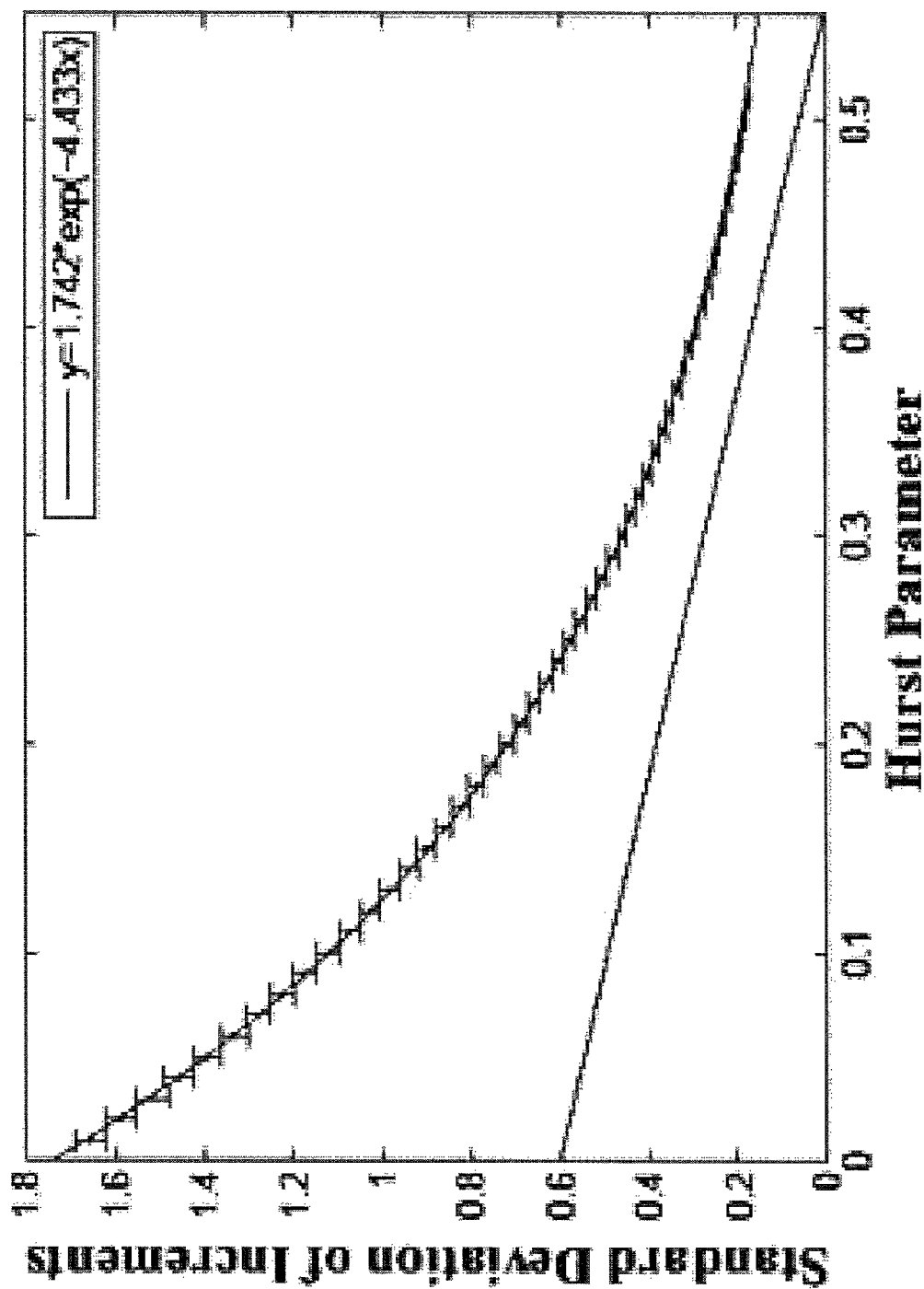
FIG. 4 is a graph illustrating the accuracy with which Hurst parameters can be recovered using systems and methods according to embodiments disclosed herein.

FIG. 4 is a graph illustrating the accuracy with which Hurst parameters can be recovered using systems and methods according to embodiments disclosed herein. The Hurst parameter is one of the two parameters of a particular stochastic process called fractional Brownian motion (fBm). FIG. 4 shows that in the case of a fBm model, the Hurst parameter values used to create the simulated data can be recovered with a high degree of accuracy. FIG. 4 shows the mean standard deviation of 1000 simulated path increments for each Hurst parameter, $H \in \{0.1:0.01:0.501\}$. The straight line is for reference and has a slope of −1.

V. Results

Figure 5:
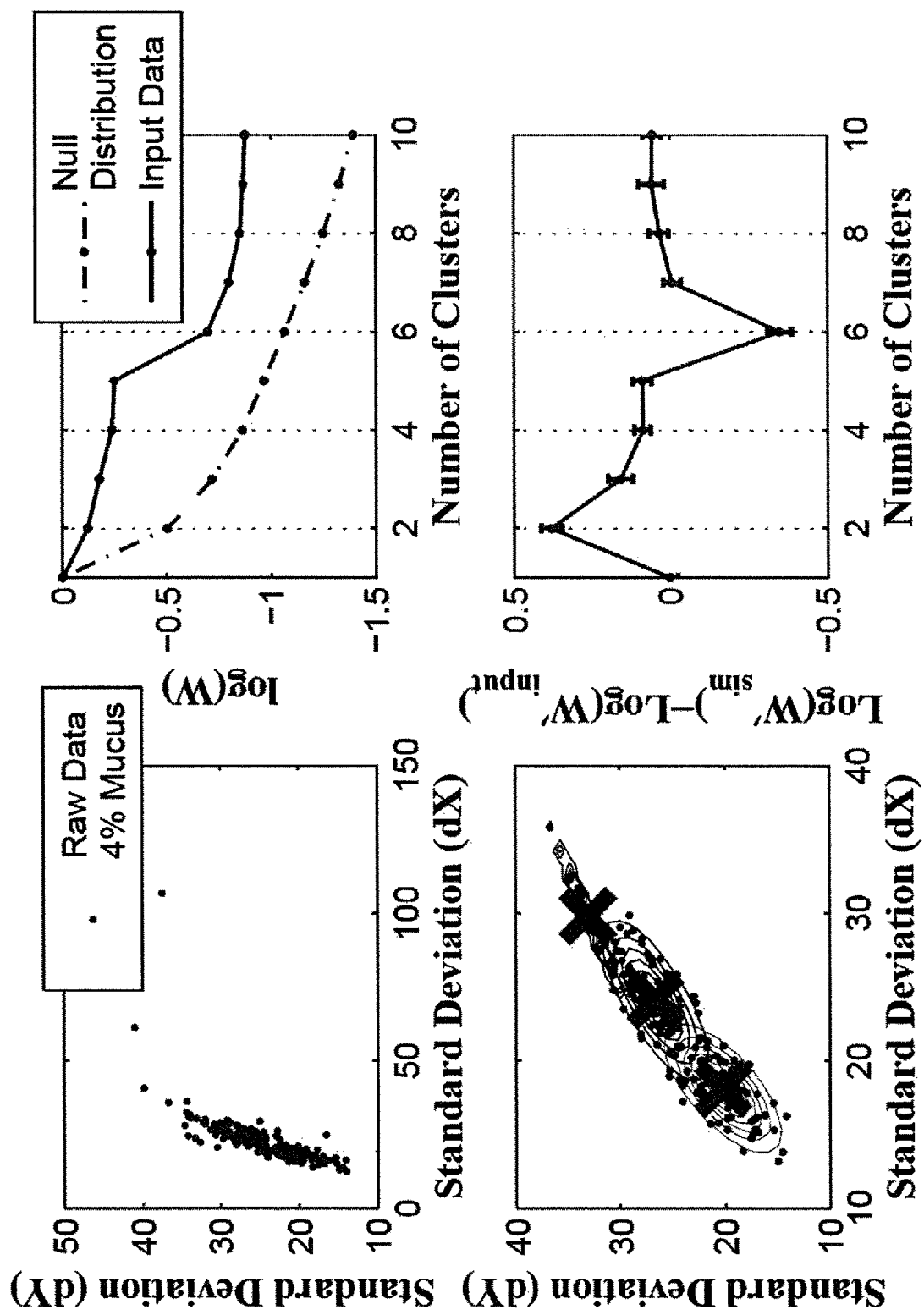
FIG. 5 is a graph illustrating position and time data collected for 180 1 μm particles undergoing passive thermal diffusion in 4% mucus.

Simulated Data. The initial tests were conducted on simulated data with a known number of underlying clusters. FIG. 5 illustrates PDF fitting results from 100 simulated data paths with Hurst parameters H=1 and diffusion coefficients $D=1.28\ ^{\mu m^2}/_s$, $1.488\ ^{\mu m^2}/_s$, $2.72\ ^{\mu m^2}/_s$ and $3.1\ ^{\mu m^2}/_s$. The correct number of clusters was successfully recovered, along with the Hurst parameters used to generate the clusters.

Experimental Data, Homogeneity. Position vs. time data were collected for 100 1-μm diameter particles undergoing passive thermal diffusion in 2 molar sucrose solution.

Experimental Data, Artificial Heterogeneity. Recall that in (2), particle radius (r) and viscosity (η) are both inversely proportional to diffusivity. Therefore tracking two populations of particles of different sizes in a Newtonian fluid as if they were the same size in a homogeneous fluid is functionally equivalent to single sized particles diffusing through a fluid exhibiting two distinct viscosities. Position vs time data were collected for 90 2-μm diameter particles undergoing passive thermal diffusion in 2 molar sucrose solution and combined with data from 100 1-μm diameter particles. The algorithm correctly determined the number of clusters in the data and misclassified only 7 of the 190 data points. The mean error in the estimation of H was less than 5% and the mean error in the estimation of the diffusion coefficient was less than 14%.

Experimental Data, Mucus. After successfully testing the protocol and software on simulated data and experimental data with artificially induced heterogeneity, we now apply it to human bronchial epithelial mucus. Position vs. time data were collected for 180 1 μm particles undergoing passive thermal diffusion in 4% mucus. This data is shown in FIG. 5. For the 4% mucus data, the gap statistic identifies the presence of 6 clusters. The results of the EM algorithm indicate that three of these clusters were statistically insignificant outliers.

The techniques described herein may be applied to analysis of the movement of particles through any type of mucus, mucus simulant, complex fluid or other barrier to provide medically relevant information to describe how diffusion rates vary with particle size, particle surface chemistry, fluid thickness, disease progress, course of medical treatment, etc. Accurate modeling of sub-diffusive scaling has enormous benefits that include, but are not limited to, fine-tuning dosages of medicines that are applied to mucus barriers based on mucus type and observed thickness, determining disease progression based on observed mucosal diffusion rates, modeling the effects of disease progression on mucosal diffusion rates and tailoring treatment accordingly, and modeling the efficacy of treatments that combine medicines that soften thickened mucus layers with medicines that transport chemicals through the softened mucus layers.

Rather than using conventional data analysis to fit a standard, homogenous diffusion coefficient to the observed data, the techniques described herein more accurately model real mucus barriers and other fluids as a heterogeneous system. These techniques recognize that variations in diffusion based on particle size is a good proxy for variations of diffusion based on viscosity and elasticity variations. Rather than extensive empirical data collection, numerical simulations of stochastic processes can provide data from which it can be determined how long it takes a particle to pass through mucus or other fluid layers of different thicknesses. Furthermore, these techniques can accurately model non-standard diffusion, i.e., where the MSD does not increase linearly with time.

The techniques disclosed herein have wide potential application. Medical applications include, but are not limited to, clinical and pre-clinical applications (e.g., relating to the observation and treatment of actual patients) as well as applications that may be considered "non-clinical", such as theoretical, laboratory, and research applications, such as modeling, experimentation, and analysis, and even non-medical applications.

It will be understood that various details of the subject matter described herein may be changed without departing from the scope of the subject matter described herein. Furthermore, the foregoing description is for the purpose of illustration only, and not for the purpose of limitation.

Example Embodiments

The following list of example embodiments is illustrative and not intended to be limiting.

1. A method for data analysis and inference of particle diffusion in mucus barriers and generic permeable biomaterials, the method comprising: collecting experimental data of observed particle movement through samples of a target that comprises a target material or target material simulant; analyzing the collected data to determine at least one stochastic diffusive process that is being observed for particular particles in the particular sample; using one or more of the at least one observed stochastic diffusive process to simulate the diffusion of particles through the target; using the simulation results to determine how passage time, survival functions, and hitting probabilities scale according to thickness of the target; and verifying the simulation results.

2. The method of embodiment 1 wherein the target comprises one of a mucus barrier, a mucus barrier simulant, a generic permeable biomaterial, permeable biomaterial simulant or generic fluid.

3. The method of embodiment 1 wherein collecting experimental data comprises infusing a target with particles of interest and measuring positions of the particles at discrete time intervals.

4. The method of embodiment 1 wherein analyzing the collected data comprises assessing heterogeneity of the target with respect to particle size, surface chemistry, shape, or physical properties of the fluid. (Heterogeneity can be due to particles of polydispersed radii in a homogeneous fluid or particles of identical radii in a heterogeneous fluid.)

5. The method of embodiment 1 wherein analyzing the collected data comprises clustering the data into a discrete set of distinct populations based on step size distribution.

6. The method of embodiment 5 wherein clustering the data into a discrete set of distinct populations based on step size distribution comprises calculating a path metric or metrics of the step size distributions for each particle or particle path segment, identifying populations of particles or particle path segments with similar values of the chosen path metric or metrics, and assigning particles or particle path segments with similar values of the chosen path metric or metrics to one of a plurality of clusters of particles. Examples of metrics include, but are not limited to, the standard deviation and variance of the data.

7. The method of embodiment 6 wherein each of the plurality of clusters is defined by the parameters of a probability distribution function (PDF). Examples of PDFs include, but are not limited to, Gaussian functions.

8. The method of embodiment 5 wherein clustering the data includes applying a mixture model where the number of components is equal to the number of partitions in the data found during cluster analysis.

9. The method of embodiment 8 wherein clustering the data includes using an iterative expectation-maximization algorithm.

10. The method of embodiment 1 wherein simulating the diffusion of particles through the target comprises performing a plurality of simulations, wherein each simulation simulates the movement of particles through a target of a particular thickness, and includes, for each particle simulated: using the PDF parameters of the cluster to which the particle is assigned to determine realizations of the metric or metrics from the corresponding distribution; converting the metric or metrics into parameters of the proposed model for the underlying stochastic process; using the parameter values to simulate motion for the particles obeying this stochastic process, which results in a simulated path of the particle through the target; and using the plurality of simulated paths to calculate passage time distributions/survival functions/hitting probabilities of particles through the target material of the particular thickness, wherein data from the plurality of simulations is used to calculate passage time distributions/survival functions/hitting probabilities for each of a plurality of thicknesses of the target. Parameters include, but are not limited to, Hurst parameters and fractional diffusion coefficients used in a fractional Brownian motion (fBm) model, etc.

11. The method of embodiment 10 wherein the plurality of simulated paths mimic the dynamics of actual particles diffusing through a sample of the target.

12. The method of embodiment 1 wherein verifying the simulation results experimentally comprises using the simulation data to determine relevant factors (including, but not limited to, clinically relevant, pre-clinically relevant, and medically relevant factors), making predictions regarding predicted behavior of experimental data, and determining how well the predicted behavior fit the actual behavior observed in the experimental data. In one application, for example, a pharmaceutical company that is developing a new drug delivery system (e.g., engineering nanoparticles) would benefit from using the approaches described herein to evaluate the bioavailability and biodistribution of a drug or nanoparticles prior to the start of animal or clinical drug trials.

13. The method of embodiment 1 wherein verifying the simulation results includes verifying the simulation results against at least one of: the experimental data; and data collected during a subsequent validation experiment.

14. A system for data analysis and inference of particle diffusion in a target material or target material simulant, the system comprising: a data storage device for storing collected experimental data of observed particle movement through samples of a target that comprises a target material or a target material simulant; and a hardware processor for analyzing the collected data to determine at least one stochastic diffusive process that is being observed for particular particles in the particular sample, using one or more of the at least one observed stochastic diffusive process to simulate the diffusion of particles through the target, using the simulation results to determine how passage time, survival functions, and hitting probabilities scale according to thickness of the target, and verifying the simulation.

15. The system of embodiment 14 wherein the target comprises one of a mucus barrier, a mucus barrier simulant, a generic permeable biomaterial, permeable biomaterial simulant or generic fluid.

16. The system of embodiment 14 wherein the collected experimental data was collected by infusing a target with particles of interest and measuring positions of the particles at discrete time intervals.

17. The system of embodiment 14 wherein analyzing the collected data comprises assessing heterogeneity of the target with respect to particle size, surface chemistry, shape, or physical properties of the fluid.

18. The system of embodiment 14 wherein analyzing the collected data comprises clustering the data into a discrete set of distinct populations based on step size distribution.

19. The system of embodiment 18 wherein clustering the data into a discrete set of distinct populations based on step size distribution comprises calculating a path metric or metrics of the step size distributions for each particle or particle path segment, identifying populations of particles or particle path segments with similar values of the chosen path metric or metrics, and assigning particles or particle path segments with similar values of the chosen path metric or metrics to one of a plurality of clusters of particles. Examples of metrics include, but are not limited to, the standard deviation and variance of the data.

20. The system of embodiment 19 wherein each of the plurality of clusters is defined by the parameters of a probability distribution function (PDF).

21. The system of embodiment 18 wherein clustering the data includes applying a mixture model where the number of components is equal to the number of partitions in the data found during cluster analysis.

22. The system of embodiment 21 wherein clustering the data includes using an iterative expectation-maximization algorithm.

23. The system of embodiment 14 wherein simulating the diffusion of particles through the target comprises performing a plurality of simulations, wherein each simulation simulates the movement of particles through a target of a particular thickness, and includes, for each particle simulated: using the PDF parameters of the cluster to which the particle is assigned to determine realizations of the metric or metrics from the corresponding distribution; converting the metric or metrics into parameters of the proposed model for the underlying stochastic process; using the parameter values to simulate motion for the particles obeying this stochastic process, which results in a simulated path of the particle through the target; and using the plurality of simulated paths to calculate passage time distributions/survival functions/hitting probabilities through the target of the particular thickness, wherein data from the plurality of simulations is used to calculate passage time distributions/survival functions/hitting probabilities for each of a plurality of thicknesses of the target. Parameters include, but are not limited to, Hurst parameters and fractional coefficients used in a fractional Brownian motion (fBm) model, etc.

24. The system of embodiment 23 wherein the plurality of simulated paths mimic the dynamics of actual particles diffusing through a sample of the target.

25. The system of embodiment 14 wherein verifying the simulation results experimentally comprises using the simulation data to determine relevant factors, making predictions regarding predicted behavior of experimental data, and determining how well the predicted behavior fit the actual behavior observed in the experimental data.

26. The system of embodiment 14 wherein verifying the simulation results includes verifying the simulation results against at least one of: the experimental data; and data collected during a subsequent validation experiment.

27. A non-transitory computer readable medium having stored thereon executable instructions that when executed by the processor of a computer control the computer to perform steps comprising: collecting experimental data of observed particle movement through samples of a target that comprises a target material or target material simulant; analyzing the collected data to determine at least one stochastic diffusive process that is being observed for particular particles in the particular sample; using one or more of the at least one observed stochastic diffusive process to simulate the diffusion of particles through the target; using the simulation results to determine how passage time scales according to thickness of the target; and verifying the simulation results.

What is claimed is:

1. A method for data analysis and inference of particle diffusion in mucus barriers and permeable biomaterials, the method comprising:
   collecting experimental data of observed movements of particles through samples of a target material, wherein collecting the experimental data includes using video microscopy and particle tracking software to capture changes in particle positions over time in the samples, wherein the samples comprise mucus or permeable biomaterial samples;
   grouping the particles into a number of distinct clusters based on the observed movements of particles;
   analyzing the changes in particle positions over time to determine, for each cluster, a stochastic diffusive process that is being observed for particular particles in the cluster and parameters of the stochastic diffusive process, wherein the parameters of the stochastic diffusive process of each cluster are sampled from a Gaussian distribution that is determined, using an expectation maximization algorithm, to have generated the cluster;
   using the stochastic diffusive processes for the clusters to simulate diffusion of particles through the target material, wherein simulating the diffusion of particles through the target material comprises performing a plurality of simulations, wherein each simulation simulates movement of particles through a target material of a particular thickness, and includes, for each particle simulated:
     using parameters of the Gaussian distribution of the cluster to which the particle is assigned to determine standard deviations from the Gaussian distribution;
     converting the standard deviations into Hurst parameter and pre-factor values;
     using the Hurst parameter and pre-factor values to simulate fractional Brownian motion for the particle, which results in a simulated path of the particle through the target material: and
   using the plurality of simulated paths to calculate passage time distributions through the target material of the particular thickness, wherein data from the plurality of simulations is used to calculate passage time distributions for each of a plurality of thicknesses of the target material;

using results from the simulating to model passage times of the particles in the target material as a function of layer thickness of the target material; and predicting, using the modeling of the passage times determined from the results from the simulating, uptake of a drug or nanoparticles in the target material prior to a start of animal or clinical drug trials involving administering the nanoparticles or the drug to subjects through the target material.

2. The method of claim 1 wherein collecting experimental data comprises infusing the samples with particles of interest and measuring positions of the particles at discrete time intervals.

3. The method of claim 1 wherein analyzing the collected data comprises assessing heterogeneity of the target material with respect to particle size.

4. The method of claim 1 wherein the clusters comprise distinct populations of particles that differ from populations of particles in other clusters based on particle movement step size distribution.

5. The method of claim 4 wherein grouping the particles into a number of distinct clusters comprises calculating standard deviations of step size distributions for each particle, identifying populations of particles with similar standard deviations, and assigning particles with similar standard deviations to one of the clusters.

6. The method of claim 4 wherein grouping the particles into distinct clusters comprises applying a Gaussian mixture model where a number of Gaussian distributions is equal to the number of distinct clusters.

7. The method of claim 6 wherein the expectation maximization algorithm comprises an iterative expectation maximization algorithm.

8. The method of claim 1 wherein using results from the simulating further comprises using simulation data to determine clinically relevant factors, make predictions regarding predicted behavior of experimental data, and determine how well the predicted behavior fits an actual behavior observed in the experimental data.

9. The method of claim 1 comprising verifying the results from the simulating against at least one of:

the experimental data; and data collected during a subsequent validation experiment.

10. The method of claim 1 wherein collecting experimental data of observed movements of particles through samples of a target material includes collecting experimental data of movements of particles of different diameters though the target material.

11. A system for data analysis and inference of particle diffusion in mucus barriers and permeable biomaterials, the system comprising:

a data storage device for storing collected experimental data of observed movements of particles through samples of a target material, wherein the collected experimental data includes data generated by particle tracking software through analysis of video microscopy data and indicating changes in particle positions over time in the samples, wherein the samples comprise mucus or permeable biomaterial samples; and a hardware processor for grouping the particles into a number of distinct clusters based on the observed movements of particles, analyzing the collected experimental data to determine, for each cluster, a stochastic diffusive process that describes the observed particle movement in the mucus or permeable biomaterial of particles in a cluster and parameters of the stochastic diffusive process, wherein the parameters of the stochastic diffusive process of each cluster are sampled from a Gaussian distribution that is determined, using an expectation maximization algorithm, to have generated the cluster, wherein the hardware processor is further configured for using the stochastic diffusive processes for the clusters to simulate diffusion of particles through the target material, using results from the simulating to model passage time distributions of the particles in the target material as a function of layer thickness of the target material and predicting, using the modeling of the passage time distributions determined from the results from the simulating, uptake of a drug or nanoparticles in the target material prior to a start of animal or clinical drug trials involving administering the nanoparticles or the drug to subjects through the target material, wherein simulating the diffusion of particles through the target material comprises performing a plurality of simulations, wherein each simulation simulates movement of particles through a target material of a particular thickness, and includes, for each particle simulated:

using parameters of the Gaussian distribution of the cluster to which the particle is assigned to determine standard deviations from the Gaussian distribution;

converting the standard deviations into Hurst parameter values;

using the Hurst parameter and pre-factor values to simulate fractional Brownian motion for the particle, which results in a simulated path of the particle through the target material; and using the plurality of simulated paths to calculate passage time distributions through the target material of the particular thickness, wherein data from the plurality of simulations is used to calculate passage time distributions for each of a plurality of thicknesses of the target material.

12. The system of claim 11 wherein the collected experimental data was collected by infusing the samples with particles of interest and measuring positions of the particles at discrete time intervals.

13. The system of claim 11 wherein analyzing the collected data comprises assessing heterogeneity of the target material with respect to particle size.

14. The system of claim 11 wherein the clusters comprise distinct populations of particles that differ from populations of particles in other clusters based on particle movement step size distribution.

15. The system of claim 14 wherein grouping the data into distinct populations based on step size distribution comprises calculating standard deviations of step size distributions for each particle, identifying populations of particles with similar standard deviations, and assigning particles with similar standard deviations to one of the clusters of particles.

16. The system of claim 14 wherein grouping the particles into clusters comprises applying a Gaussian mixture model where a number of Gaussian distributions is equal to the number of distinct clusters.

17. The system of claim 16 wherein the expectation maximization algorithm comprises an iterative expectation maximization algorithm.

18. The system of claim 11 wherein using results from the simulating further comprises using simulation data to determine clinically relevant factors, make predictions regarding predicted behavior of experimental data, and determine how well the predicted behavior fits an actual behavior observed in the experimental data.

19. The system of claim 11 comprising verifying the results from the simulating against at least one of:
the experimental data; and
data collected during a subsequent validation experiment.

20. The system of claim 11 wherein the collected experimental data of observed movements of particles through samples of a target material includes experimental data of movements of particles of different diameters though the target material.

21. A non-transitory computer readable medium having stored thereon executable instructions that when executed by a processor of a computer control the computer to perform steps comprising:
collecting experimental data of observed movements of particles through samples of a target material, wherein collecting the experimental data includes using video microscopy and particle tracking software to capture changes in particle positions over time in the samples, wherein the samples comprise mucus or permeable biomaterial samples;
grouping the particles into distinct clusters based on the observed movements of particles;
analyzing the changes in particle positions over time to determine, for each cluster, a stochastic diffusive process that approximates particle statistics for particles in the cluster and parameters of the stochastic diffusive process, wherein the parameters of the stochastic diffusive process of each cluster are sampled from a Gaussian distribution that is determined, using an expectation maximization algorithm, to have generated the cluster;
using the stochastic diffusive processes for the clusters to simulate diffusion of particles through the target material, wherein simulating the diffusion of particles through the target material comprises performing a plurality of simulations, wherein each simulation simulates movement of particles through a target material of a particular thickness, and includes, for each particle simulated:
using parameters of the Gaussian distribution of the cluster to which the particle is assigned to determine standard deviations from the Gaussian distribution;
converting the standard deviations into Hurst parameter and pre-factor values;
using the Hurst parameter and pre-factor values to simulate fractional Brownian motion for the particle, which results in a simulated path of the particle through the target material; and
using the plurality of simulated paths to calculate passage time distributions through the target material of the particular thickness, wherein data from the plurality of simulations is used to calculate passage time distributions for each of a plurality of thicknesses of the target material;
using results from the simulating to model passage time distributions of the particles in the target material as a function of layer thickness of the target material; and
predicting, using the modeling of the passage time distributions determined from the results from the simulating, uptake of a drug or nanoparticles in the target material prior to a start of animal or clinical drug trials involving administering the nanoparticles or the drug to subjects through the target material.

22. The non-transitory computer readable medium of claim 21 wherein collecting experimental data of observed movements of particles through samples of a target material includes collecting experimental data of movements of particles of different diameters though the target material.

* * * * *